(12) United States Patent
Reinhard et al.

(10) Patent No.: US 6,331,174 B1
(45) Date of Patent: Dec. 18, 2001

(54) PREFILLED, LOW PARTICLE, STERILE DISPOSABLE SYRINGE FOR INJECTING PREPARATIONS AND PROCEDURE FOR MANUFACTURE

(75) Inventors: Michael Reinhard, Ober-Olm; Michael Spallek, Ingelheim, both of (DE)

(73) Assignee: Schott Glaswerke (DE)

(*) Notice: Subject to any disclaimer, the term of this patent is extended or adjusted under 35 U.S.C. 154(b) by 926 days.

(21) Appl. No.: 08/529,195

(22) Filed: Sep. 15, 1995

(30) Foreign Application Priority Data

Oct. 27, 1994 (DE) .................................. 44 38360

(51) Int. Cl.<sup>7</sup> ...................................................... A61M 5/00
(52) U.S. Cl. ..................... 604/232; 427/2.3; 604/199; 604/265; 604/230
(58) Field of Search ..................................... 604/239, 240, 604/192, 265, 218, 230, 232, 199; 427/2.3

(56) References Cited

U.S. PATENT DOCUMENTS

| | | | |
|---|---|---|---|
| 2,512,568 | * 6/1950 | Saffir | 604/239 |
| 3,330,004 | 7/1967 | Cloyd et al. | |
| 4,633,765 | * 1/1987 | Knödel | 604/230 |
| 4,814,231 | * 3/1989 | Onohara et al. | 604/265 X |
| 4,820,278 | * 4/1989 | Balisky | 604/218 |
| 5,135,514 | 8/1992 | Kimber | |
| 5,147,328 | * 9/1992 | Dragosits et al. | 604/218 |
| 5,246,423 | 9/1993 | Farkas | |
| 5,270,012 | * 12/1993 | Opolski | 604/265 X |
| 5,441,988 | * 8/1995 | Shimura et al. | 604/265 |
| 5,468,562 | * 11/1995 | Farivar et al. | 428/457 |
| 5,478,324 | * 12/1995 | Meyer | 604/203 |

FOREIGN PATENT DOCUMENTS

| | | |
|---|---|---|
| 29 39 180 C2 | 4/1980 | (DE) . |
| 30 49 612 A1 | 7/1982 | (DE) . |
| 3916101 | 11/1990 | (DE) . |
| 0556034 | 8/1993 | (EP) . |
| WO9415581 | 7/1994 | (WO) . |
| WO9512482 | 5/1995 | (WO) . |

OTHER PUBLICATIONS

Derwent Publications Ltd., Abstract for JP-A-62 137 065 of ISONO.

* cited by examiner

Primary Examiner—Anhtuan T. Nguyen
(74) Attorney, Agent, or Firm—George T. Marcou; Kirkpatrick Stockton LLP

(57) ABSTRACT

Prefilled, disposable syringes for injecting preparations with a fill volume of less than 5 ml are typically made of glass. The disposable syringe in this invention avoids the use of glass as a construction material. The body of the syringe with barrel, grip and nozzle is made of transparent, glass-like plastic with a very low gas permeability and is designed to be resistant to gamma rays and/or ethylene oxide gas, whereby the hypodermic needle is directly integrated within the plastic nozzle.

20 Claims, 7 Drawing Sheets

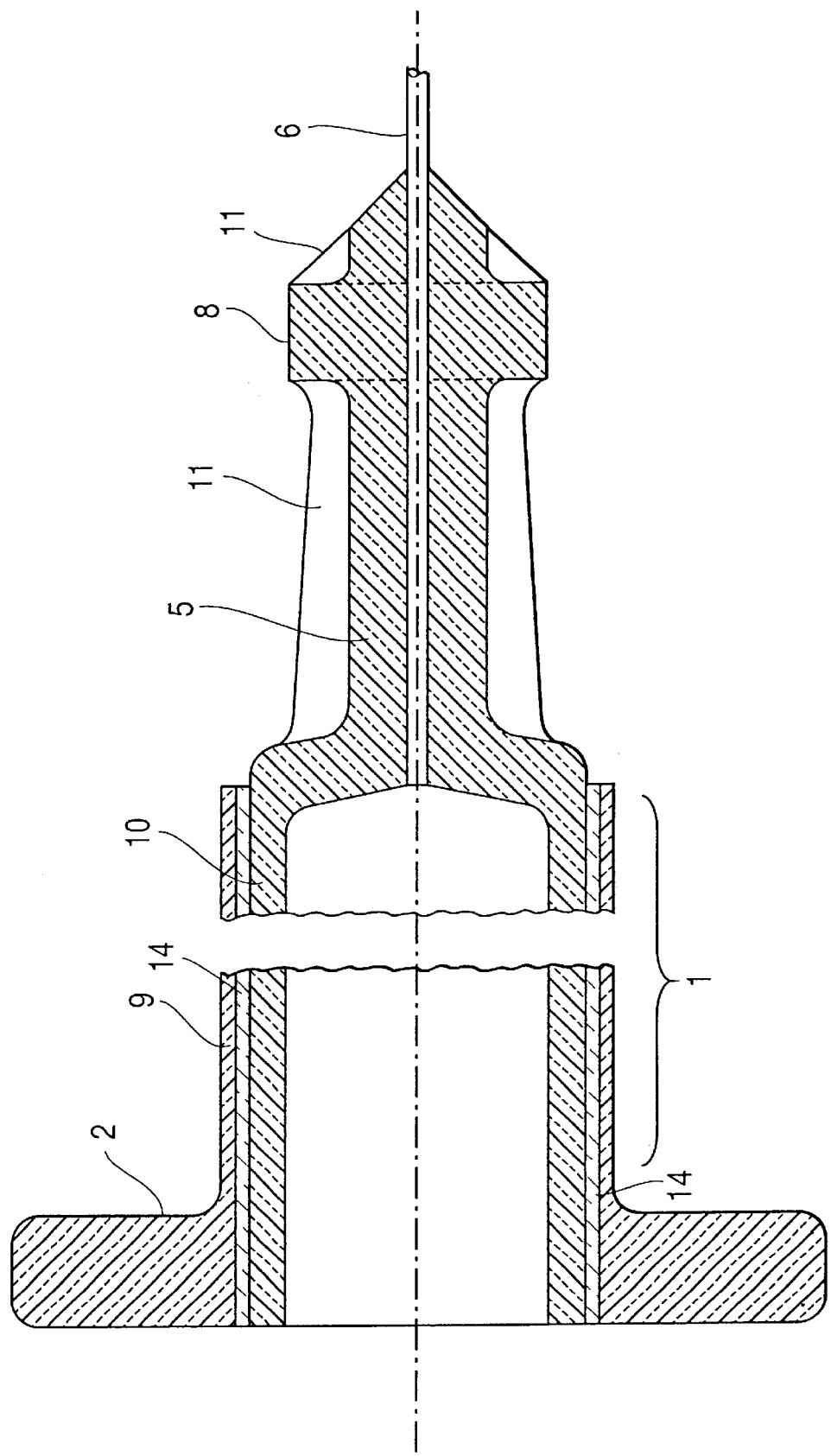

PREFILLED, LOW PARTICLE, STERILE DISPOSABLE SYRINGE FOR INJECTING PREPARATIONS AND PROCEDURE FOR MANUFACTURE

BACKGROUND OF THE INVENTION

1. Field of the Invention

The present invention generally relates to a prefilled, low particle, sterile, disposable syringe for injecting preparations with a fill volume of less than 5 ml. More particularly, the present invention relates to a syringe comprising a main body and a hypodermic needle, the body of the syringe being comprised of a grip, a nozzle, and a barrel equipped with an interior lubricating layer and an open end to accommodate a plunger that can be moved by means of a plunger rod within the barrel, and the hypodermic needle being mounted firmly within the nozzle, such that the needle penetrates the protective cap, forming a seal, while at the same time the interior of the cap sleeve fits tightly against the nozzle, also sealing the exterior surface of the needle. Furthermore, the invention concerns a procedure for the manufacture of such a syringe.

2. Description of the Prior Art

Prefilled, sterile, disposable syringes for medicinal purposes combine two different functions. On the one hand, they are suitable for storing highly effective preparations over a period of several years; on the other hand, they are also the instrument used to administer the preparations directly to the patient. Whereas in the case of vials and ampoules, preparations can only be administered after having first been drawn from the container by means of an empty syringe. The use of a prefilled, disposable syringe eliminates this filling process, i.e., pulling the plunger. In this way, the energy expended and the risks of confusing and of contaminating preparations are considerably reduced. In addition, when considering the "Total Cost of Drug Delivery," administering preparations directly from the container represents by far the most economical possibility.

Up to now only one example is known of a prefilled, disposable syringe of the type described in the introduction: the SCF (Sterile Clean Fill)—Staked Needle Injection by Becton Dickinson. The body of the syringe, i.e., the barrel, the grip, and the nozzle, consists of a single glass part, and for this reason the syringe is also called a prefilled, disposable glass syringe. Certainly in all known disposable syringes for injections of <5 ml, the barrel at the very least is made of glass.

The needle of an SCF—Staked Needle Injection is glued into a corresponding recess in the nozzle. Disposable glass syringes are also known (e.g., German Patent Nos. DE 2,939,180 C2 and DE 3,916,101) in which the hypodermic needle is not directly integrated in the nozzle, but rather, is glued into an additional piece that can be mechanically connected to the nozzle. This increases the number of pieces and introduces an additional seam which must be sealed.

A major disadvantage of the disposable glass syringe is the risk of breakage and the related risks of injury and infection. Furthermore, many types of glass are not suitable for gamma ray sterilization, as the glass becomes permanently discolored. Gamma ray sterilization is, however, a very simple, economical and harmless sterilization procedure.

A further disadvantage of the disposable glass syringe is the costly procedure necessary to manufacture the glass components and to transfer them to a low particle, sterile environment. The manufacturing process for the glass components is slow and only allows for computer control and inspection in the beginning. The uncertainty of the process is equally as large. In addition to this, the glass components are continually in contact with equipment and lubricants, making a wash step absolutely necessary. The corresponding wash equipment requires a large capital investment and is expensive to operate.

Prefilled, disposable plastic syringes with total fill volumes of at least 50 ml are also known. Mallinckrodt's disposable hypodermic syringe, known under the brand name OPTIRAY, is not equipped with a hypodermic needle. Instead, infusion tubing is mechanically mounted on the nozzle. The plastic consists of (translucent) polypropylene.

The plastic barrel of the disposable syringe found in U.S. Pat. No. 4,861,335 is equipped with a plastic cap on the side of the barrel turned away from the plunger. The hypodermic needle is fastened to the cap by means of a mounting method known under the brand name LUER-LOCK. Therefore, the needle is not integrated with the nozzle.

For injections of considerably less than 50 ml, particularly for fill volumes smaller than 5 ml, the surface of the syringe is so large in comparison to the dispensed volume that the known prefilled plastic syringes could not be stored for long periods of time. The loss of preparation components from diffusion, particularly of water as a solvent, would be so great that the change in composition would be unacceptable. Furthermore, known plastic syringes are constructed from a translucent plastic, permitting only limited visual inspection of the syringe contents, which is an important step for low volume, prefilled disposable syringes. For this reason, only prefilled, disposable glass syringes are known for fill volumes under 5 ml.

SUMMARY OF THE INVENTION

The task underlying this invention is to create a prefilled, disposable syringe that has a considerably lower risk of breakage and injury as compared to glass models, is an effective barrier against water vapor diffusion, permits the visual inspection of the dispensed preparation, and is especially simple, controllable and economical to manufacture as a preassembled unit consisting of a barrel with an integrated needle and an attached protective cap, all in a low particle, sterile package.

The solution to this task is successful in that the invention of the low volume, prefilled disposable syringe described in the introduction has the following properties: the body of the syringe is made of plastic and can be sterilized by gamma rays and/or ethylene oxide without affecting chemical or physical properties (particularly brittleness and color in the case of the syringe body) in such a way as to impair its function; the protective cap can be sterilized by gamma rays and/or ethylene oxide without affecting chemical or physical properties in such as way as to impair its function; the walls of the barrel and nozzle are designed in such a way that their permeability to water vapor is less than 0.08 $g/(m^2 \times d)$ relative to a wall thickness of 500 $\mu m$; the walls are, at least in the barrel area, transparent like glass; and the hypodermic needle is directly integrated in the nozzle.

Due to the measures taken in this invention, a prefilled, sterile, disposable syringe of the type described in the introduction has been created for a small volume which, despite the use of plastic as construction material, can be stored for long periods of time and allows for visual inspection of the syringe contents for precipitates, impurities, etc. In other words, the syringe possesses all of the advantages of the disposable glass syringe, yet without having to tolerate the disadvantages in handling and preparation caused by the use of glass as a construction material.

Handling of the syringe when dispensing the syringe contents is significantly safer than when using a disposable glass syringe.

With regard to the manufacturing process for the prefilled, sterile disposable syringe in this invention, the solution to the aforementioned task is successful in that: the plastic body of the syringe is produced in a clean room (low particle environment) by injection molding, the needles and protective caps are brought into a clean environment in the clean room and mounted on the body of the syringe in the clean room, the lubricating layer within the barrel of the syringe is applied inside the clean room, and the preassembled syringe unit, stored in a container in the clean room, is sealed in particle and bacteria-proof packaging. The body of the syringe does not undergo a previous wash step, and the container, together with its contents, is sterilized with gamma rays and ethylene oxide outside of the clean room.

This manufacturing process for the preassembled unit (consisting of the syringe body with integrated needle and attached protective cap) in low particle, sterile packaging is especially simple, controllable and economical. It is also easier to automate than the known process. The preassembled unit is then delivered to the pharmacist, who fills and finishes assembling the syringe barrel (inserts the plunger), with no need for additional costly steps in the process.

One development of the disposable syringe in this invention lies in the nozzle area where the hypodermic needle is fastened. The nozzle is constructed to encase the needle, which has an advantage over known finished glass syringes with a glued-in needle, so that no adhesive can interact with the preparation. This is especially important for highly sensitive preparations.

The closed linkage caused by friction between the needle and its casing is generally sufficient to guarantee secure attachment of the hypodermic needle. It is nevertheless advantageous for the hypodermic needle to have a profiling or a distortion (s-shaped, for instance) to produce a positive locking of the needle position. In this instance there are numerous possibilities available for achieving a variation of the straight, thin, cylindrical form, even to the point of effecting a bulge in the needle.

As an alternative to encasing the needle in the nozzle, another version of the invention has the needle glued into a recess in the nozzle. This disposable syringe can be used for less sensitive preparations and has the advantage of lower production costs. Injection molding with no inserted components simplifies equipment set up and facilitates possible shorter cycle times. Subsequent gluing of the needle is achieved using high clock rates.

A further development of this invention lies in the nozzle area where the hypodermic needle is fastened. Here, support elements (more specifically, ridges) are molded onto the nozzle, a construction which makes possible smaller accumulations of plastic around the nozzle and thus shorter cycle times during injection molding.

It is also an advantage if the nozzle surface on which the sleeve of the protective cap forms a seal is constructed as a collar. A collar ensures that the protective cap seals cleanly. The ridges mentioned previously not only serve as supports, but also guide the rim of the protective cap over the collar.

One advancement of the invention is characterized by the body of the syringe having at least a syringe barrel consisting of an inner and outer layer of different types of plastic. Constructing the barrel and, likewise, the nozzle out of two layers of plastic is an advantage if the preparation is, for example, sensitive to oxygen or carbon dioxide. In general, plastics acting as an effective water vapor barrier have correspondingly poor resistance to gases such as oxygen and carbon dioxide. A double-layer composite structure may therefore be necessary.

According to a preferred design for this invention, the plastic used in the production of the syringe body consists of a cyclic olefin copolymer (COC). The use of a cyclic olefin copolymer is advantageous because this material offers an excellent barrier against water vapor and at the same time is transparent like glass.

According to further developments of this invention, it is also an advantage to provide another layer of metallic, ceramic or glass-like material, which forms a functional boundary between the plastic, providing form and acting as a structural material, and the coating material, which offers the properties of a barrier. For designs with two plastic layers, this additional layer is embedded between the plastic layers, protecting it from scratching or peeling. A design with an inner layer has the advantage that the barrier effect is obtained directly on the surface in contact with the preparation. A design with an exterior layer ensures that, even in the event that the layer peels, no particles from that layer will reach the preparation.

These various designs, as well as other advantages of the invention, will be described in conjunction with the sample designs presented in the drawings.

BRIEF DESCRIPTION OF THE DRAWINGS

FIG. 3A shows a longitudinal section of the design of FIG. 3 further including a middle layer.

DETAILED DESCRIPTION OF THE PREFERRED EMBODIMENT

Figure 1:
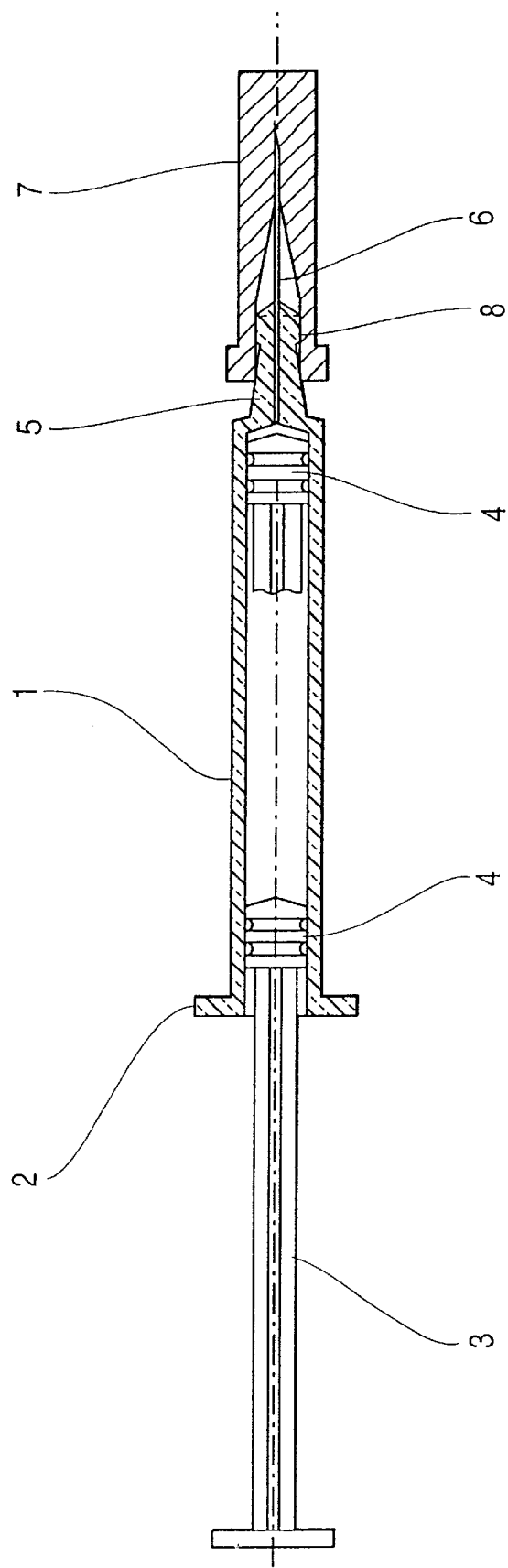
FIG. 1 shows a longitudinal section of a fully assembled, prefilled, disposable syringe for medicinal purposes.

FIG. 1 shows a longitudinal section of a prefilled, sterile, disposable syringe for medicinal purposes having a fill volume of less than 5 ml. According to one design, the fill volume of the prefilled, sterile, disposable syringe in this invention lies preferably within the range of 0.2–1 ml. There is a high demand in the medical community for syringes in this range. They are needed, for example, for the administration of heparin solutions. The body of the syringe consists of a barrel (1) with a grip (2) at one end. Within the barrel (1) is a plunger (4) which can be pulled through the barrel by means of a plunger rod (3). When the syringe is prefilled and fully assembled, the plunger (4) is located near the grip (2). After dosing, the plunger (4) is located at the other end of the syringe barrel, as shown in FIG. 1.

At this end of the syringe, the barrel turns into the nozzle (5), at which point, as will be explained, a hypodermic needle (6) is firmly fastened, i.e., not removable without damage. This hypodermic needle (6) can be covered by a protective cap (7). The nozzle (5) has, in addition, a collar (8), which can be more clearly discerned from FIG. 3. The sleeve of the protective cap (7) seals onto the cylindrical surface of the collar (8).

There are a number of alternatives available for the construction of the protective cap (7). This cap can, for instance, be made from an elastomer, primarily rubber, and the wall thickness then selected so that, when the cap is put in place, the tip of the cannula (6) penetrates the cap material, forming a seal. It is also conceivable to make a plastic cap out of relatively hard elastic material, which is then, at least in the interior area around the tip of the needle, coated with a soft elastic material that would form a seal. In this way, the soft elastic material can be selected on the basis of optimum sealing properties (sealing function), while the hard elastic material is better suited to counteract external, physical damage (protective function).

The barrel of the syringe (1) with the integrated grip (2) and nozzle (5), as well as the plunger rod (3) are made of plastic, whereas the hypodermic needle (6), as usual, is made of a metallic material and the plunger (4) of a soft elastic material. The walls of the barrel (1) and the nozzle (5) have a permeability to water vapor of less than 0.08 $g/(m^2 \times d)$ relative to a wall thickness of 500 $\mu$m. This low permeability to gas can be achieved by selecting an appropriate type of plastic. Depending on demand, a multilayer construction is also possible as shown, for example, in FIG. 3. This multilayer construction will be explained later in more detail. The walls of the syringe have, at least in the barrel area, a transparent, glass-like section, so that the contents of the prefilled syringe can be visually inspected at any time for possible contamination or precipitates. Furthermore, for the body of the syringe and the protective cap, a material is selected that can be sterilized by gamma rays and/or ethylene oxide, without affecting chemical or physical properties in such a way as to impair their function.

The hypodermic needle (6) in the sample design in FIG. 1 (and FIG. 3) is held in place by only the surrounding nozzle, without the use of additional adhesives. The collar (8) shape of the nozzle surface, which forms a seal with the protective cap (7), only leads to small accumulations of material in the area surrounding the needle. The plastic encasing the needle is therefore designed to be thin, allowing it to shrink after molding around the needle. In this way, a sufficient sealing and bonding effect can be achieved while the plastic cools after injection into the mold. This effect becomes particularly noticeable in the design shown in FIG. 3 where the area surrounding the needle is relatively thin and has support ribs (11).

Figure 2:
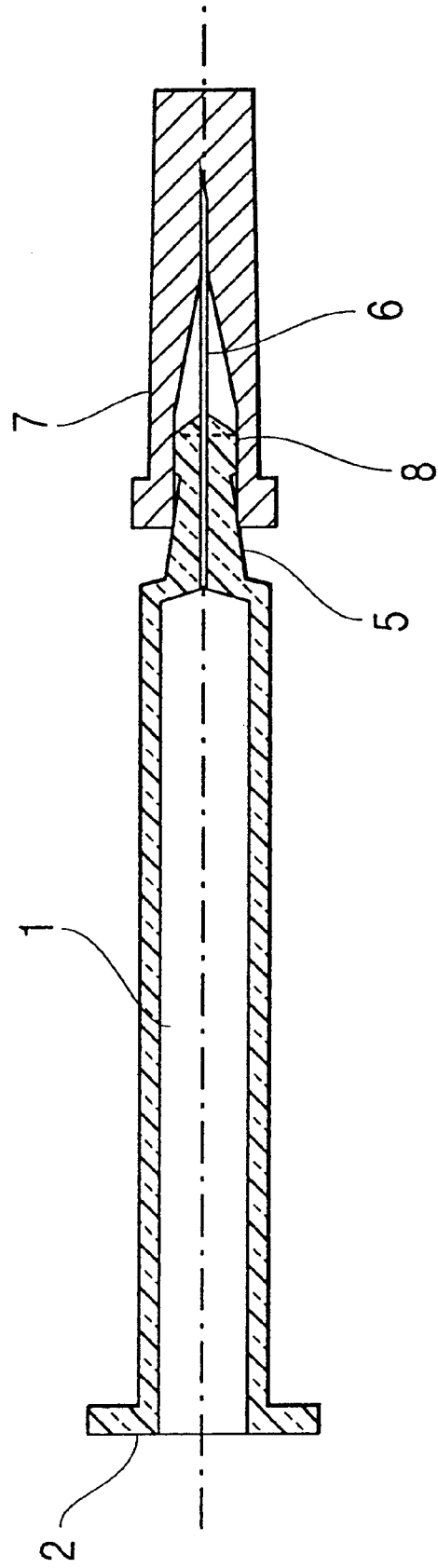
FIG. 2 shows a longitudinal section of a preassembled unit consisting of the body of the syringe, integrated needle and attached protective cap.

The prefilled, fully assembled, disposable syringe in FIG. 1 consists of a preassembled unit with a syringe body (1,2,5), an integrated needle (6), and a protective cap (7) on the one hand, as well as the plunger (4) and plunger rod (3) on the other hand. For the sake of clarity, the preassembled unit is shown again separately in FIG. 2. The syringe manufacturer delivers it in an opened state (i.e., plunger and plunger rod separate) to the pharmacist, who fills the preassembled syringe and finishes the assembly.

As shown in FIG. 1, the wall of the syringe barrel (1) and nozzle (5) can be homogeneous, i.e., constructed as a single layer. The corresponding plastic must then demonstrate all of the properties required to keep the prefilled, sterile, disposable syringe fully functional. It must be compatible with the prefilled medication as well as have the necessary strength and impermeability to water vapor. The wall of the barrel and, likewise, the nozzle can nevertheless be constructed of several layers of various types of plastic. In the sample design in FIG. 3, the syringe barrel (1) consists of two different layers of plastic (9 and 10).

Figure 3:
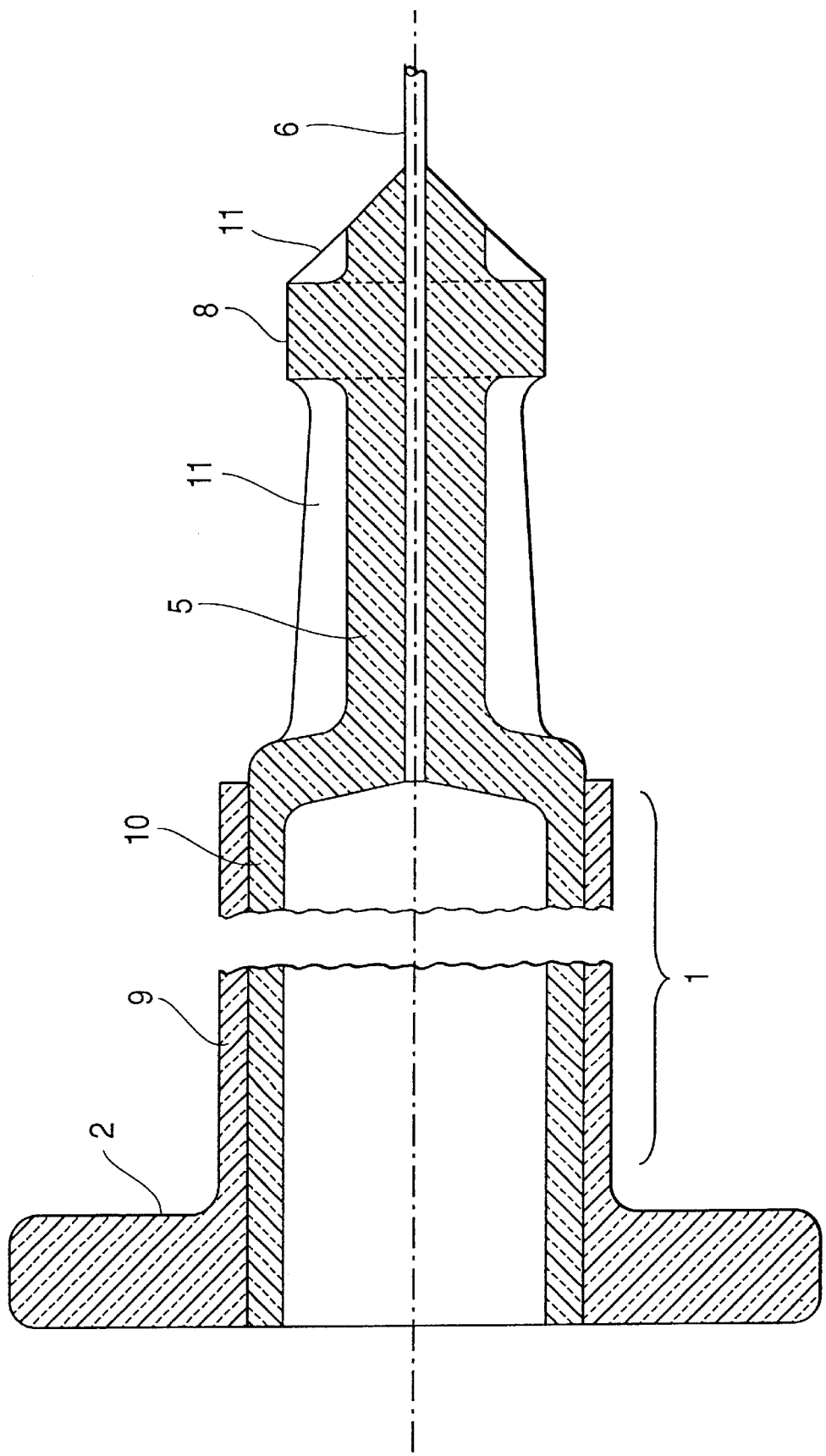
FIG. 3 shows a longitudinal section of a further design for the syringe body with the needle encased in the nozzle.

To better bring out details, a larger scale was chosen for FIG. 3, whereby, the barrel (1) is drawn with a break in the scale for presentation reasons. In the area where the needle is fastened in the nozzle (5), four ridges (11) are provided, distributed symmetrically around the perimeter. Two of these ridges are shown uncut in FIG. 3. In each case the supports extend outward from above the collar (8) up to the conical tip. These ridges or ribs (11) serve on the one hand to strengthen the area surrounding the needle and, on the other hand, to guide the edge of the protective cap (not shown) when it is set in place.

The double layer construction of the syringe barrel (FIG. 3) has the advantage that the barrier properties of the wall can be easily tailored according to the requirements of the preparation to be dispensed. In this way, for example, a type of plastic that acts as a good barrier to oxygen diffusion can be combined with one that blocks diffusion of water vapor.

Plastics that act as good barriers to water vapor diffusion are, for example, cyclic olefin copolymers, polyethylene-pentene and glass-clear polypropylene; plastics that counteract oxygen diffusion are PET, EVOH and PVDC.

A middle layer 14 made of a metallic, ceramic or glassy material, such as $SiO_x$, $SiO_xC_y$, and $TiO_xC_y$, can also be placed between the two layers of plastic as shown in FIG. 3A to act as a diffusion barrier. With a typical thickness of 50–300 nm, this type of layer has a greater resistance to diffusion than all known plastics and is substantially stronger. In this way, prefilled, disposable syringes with an inorganic middle layer between two plastic layers meet high demands with respect to their properties as diffusion barriers, and thus allow for the consideration of a larger selection of plastics.

A syringe body consisting of several layers of plastic can be manufactured using multi-component injection molding. This is itself a familiar process in which the inner layer is injected first, followed by a second step in which the first layer is coated with another plastic. Between steps it is also conceivable to plasma-treat the outer surface of the first layer in order to effect changes in the plastic surface aimed at enhancing the diffusion barrier. Adhesion-promoting layers can also be applied to the outer layer of the first body.

Furthermore, a syringe barrel and nozzle consisting of a single plastic layer construction can also be provided with an inner layer made of a metallic, ceramic or glassy material. This prevents the active substance from depositing on or migrating into the plastic. This inner layer can also be designed to enhance the ability of the plunger (4) to slide within the barrel (1). In this case, it is conceivable to construct the metallic, ceramic or glass layer in such a way that it gradually merges with a fluoropolymer layer, such as PTFE, PFA or FEP, so that the otherwise standard siliconization of the interior of the syringe barrel can be eliminated.

The aforementioned metallic, ceramic and glass layers, as well as the fluoropolymer layers can be applied by a chemical vapor deposition process (i.e., CVD, PVD, particularly plasma-CVD). This could ideally be done using injection molding equipment. Plasma polymerization layers or modifications to plastics are also possible using a plasma treatment.

The selection of layer combinations must be optimized according to the requirements of the entire packaging.

Typical requirements are high resistance to diffusion of gases ($H_2$, $O_2$, $CO_2$) both into and out of the syringe, resistance to diffusion of plastic components or label adhesive into the syringe, as well as resistance to sterilization by γ-radiation, ethylene oxide gas, or to autoclaving for longer than 20 minutes at a temperature of 121° C. When determining the sequence of layers, it must be taken into consideration that the interior layer needs to be compatible with the filling material (inertness, no adsorption or absorption of preparation components) and that the exterior layer be as scratch resistant as possible.

Figure 4:
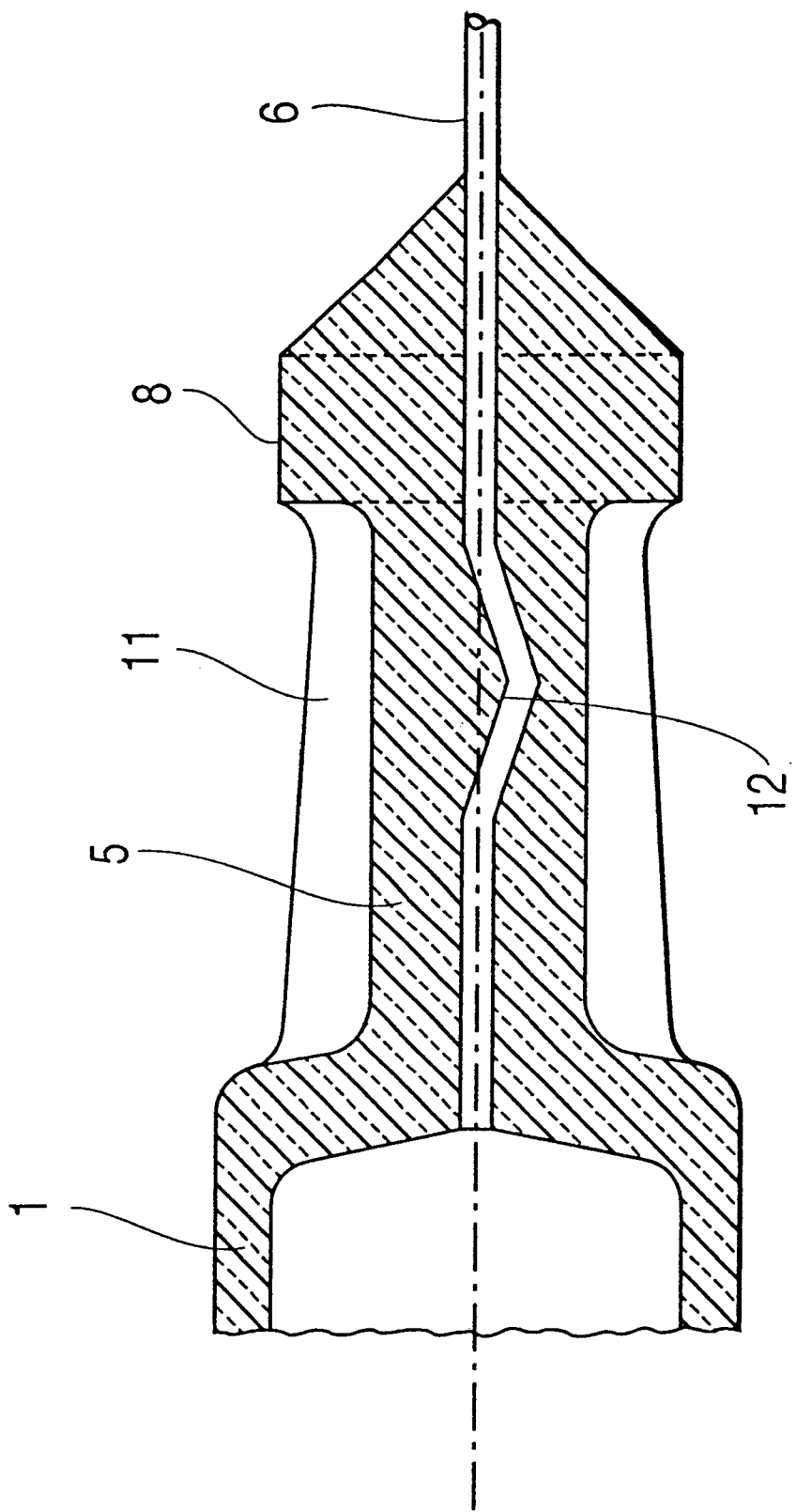
FIG. 4 shows a longitudinal section of a design for a distorted needle encased in the nozzle.

FIG. 4 shows a nozzle (5) design with an encased needle (6). Here the needle is distorted (12), providing a positive shape-conforming connection between the needle and nozzle, which ensures that the needle is not pulled out or pushed in. Other forms are possible (such as a bulge in the needle) instead of the distortion shown.

Figure 5:
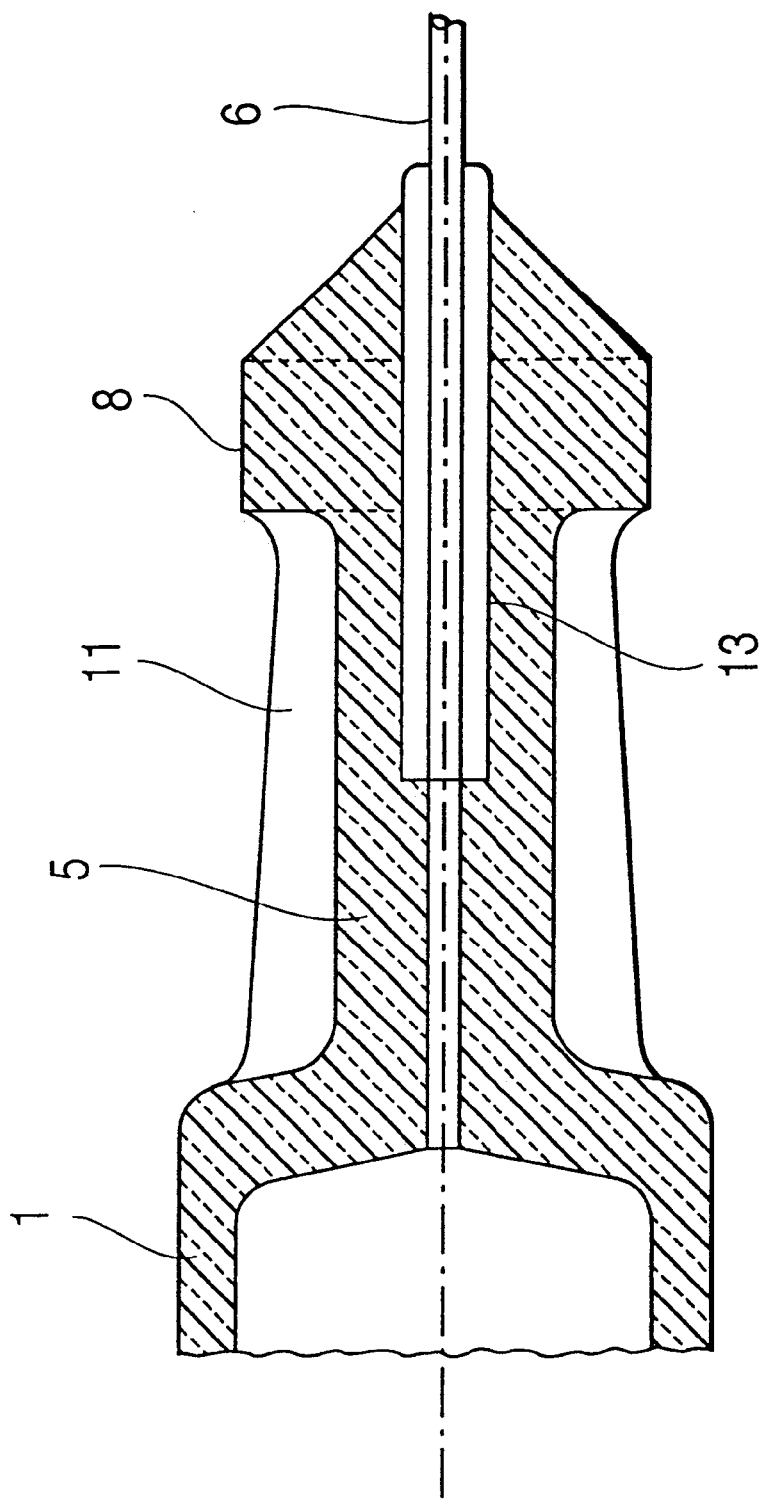
FIG. 5 shows a longitudinal section of a design for a needle glued into the nozzle.

FIG. 5 shows a design of the nozzle (5) with a recess (13) for adhesive used to secure the needle (6) in the nozzle. The adhesive area lies, as shown, only in the front section of the nozzle, maintaining a desirable distance from the syringe barrel (1). In this way, contact between the adhesive and the contents of the syringe is largely avoided.

The prefilled, disposable syringe in this invention can be manufactured, sterilized and the low particle content maintained with relative ease when compared with the state-of-the-art technology in European Patent No. 0 227 401 B1, which describes a manufacturing (and filling) process for the Mallinckrodt large volume, finished polypropylene syringe. This technology is analogous to that described for this invention.

In this familiar case, the next step is a mechanical removal of waste particles and other contaminants, as well as a sterilization step for the cap and the plunger.

The syringe barrel, with the nozzle, is washed after its production to remove waste particles and pyrogens. Then it is dried. Afterward, a lubricant is applied to the interior of the barrel.

Following this, the protective cap is set in place, the barrel is filled with the liquid to be dispensed, the plunger is inserted in the open end of the syringe body, and the entire disposable syringe is sterilized in an autoclave. These process steps are performed predominantly in the pharmacy, making the actual filling process relatively expensive.

Figure 6:
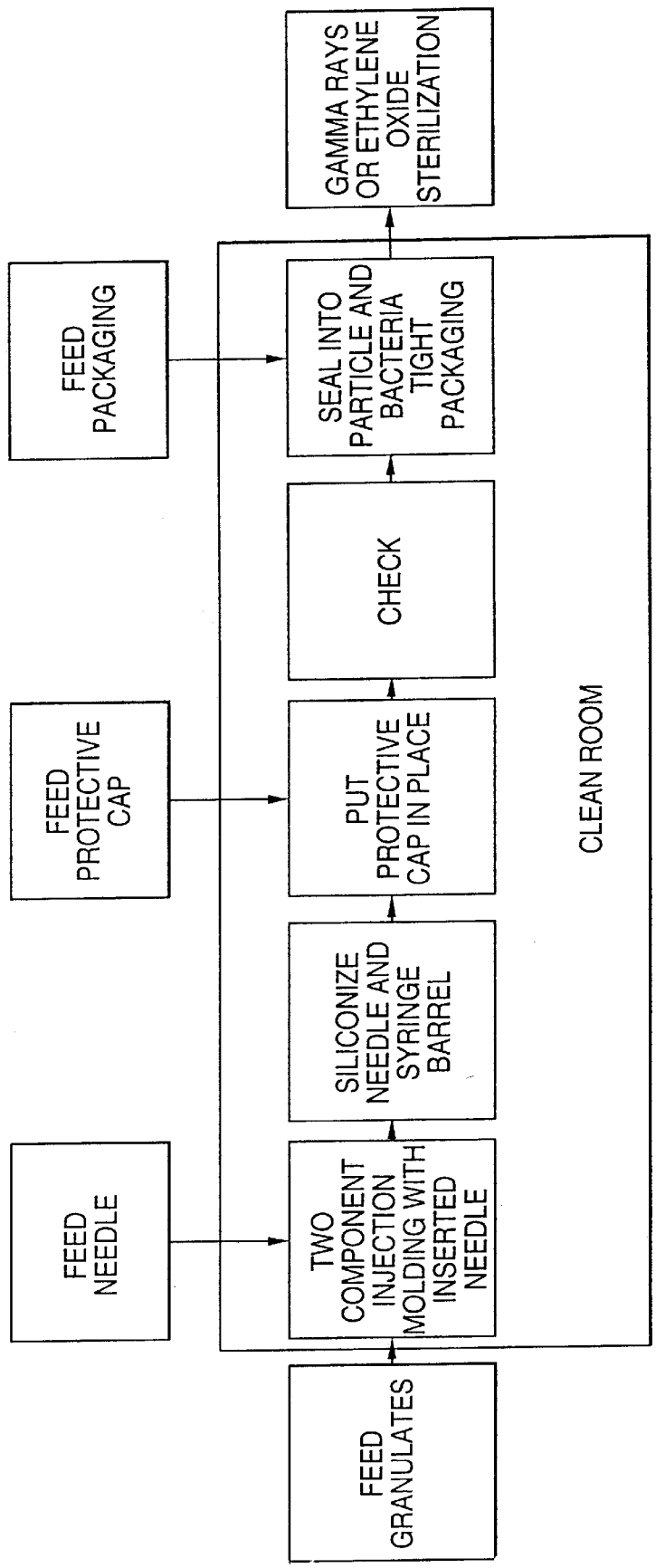
FIG. 6 shows a schematic representation of the manufacturing process for the disposable syringe in this invention.

In contrast, the production of the prefilled, sterile disposable syringe in this invention is as follows (FIG. 6):
1. The syringe body (1 and 5) with the integrated hypodermic needle (6) is produced in clean room conditions (low particle environment). The needles and protective caps are brought in a clean environment into the clean room and mounted on the body of the syringe. For designs in which the needle is encased in the nozzle, the body of the syringe with the inserted needle is produced by injection molding. If the syringe body has a double layer construction, production is undertaken using two component injection molding.
2. In the next step, a lubricating layer is applied to the interior of the syringe body under clean room conditions. Preferably, silicon oil is applied as a lubricant onto the interior of the syringe barrel by spraying, brushing, dipping or a similar process immediately after production of the barrel. It is advantageous to heat-fix the lubricant (air convection or radiation). A possible alternative is the use of a UV-polymerizing silicon oil or similar silicon emulsion.
3. This is followed by the placement of the protective needle cap (7).
4. Finally, while in the clean room, the body of the syringe is placed in a closed storage container, sealed from particles or bacteria and sterilized by gamma rays or, alternatively, by ethylene oxide gas outside of the clean room.

Afterwards—at the pharmacy—the preassembled syringe unit is filled with the preparation material to complete the assembly, i.e., the plunger and plunger rod are inserted, followed by, if necessary, autoclaving and inspection, as well as labeling and secondary packaging. Preparatory steps prior to filling, inserting the plunger and plunger rod, and further packaging are principally carried out according to the state of the art.

The advantages of the process in this invention over the known process are:
a) The complicated washing and drying of the syringe body have been eliminated, because the plastic components can be produced under clean room conditions (low particle environment). For small volume containers, it is therefore not necessary to remove pyrogens when using the present invention.
b) The silicon lubricant is coated immediately after the plastic has been molded. In this way, the heightened surface activity, which is still available shortly after production of the plastic, can be utilized to improve the adhesion of the lubricant.
c) Sterilization can be simply carried out even before the syringe is filled with the preparation. In this way, preassembled syringe units that have already been sterilized can be made available to pharmacists, substantially simplifying the process steps at the pharmacy.

What is claimed is:

1. A prefillable, low-particle, sterile, single use syringe for the injection of preparations having a filling volume of less than 5 ml, the syringe comprising:

a syringe plunger;

a piston rod connected to the syringe plunger; and a syringe body, the syringe body including:
   a syringe cylinder having a first end and a second end and inner walls defining a cylinder interior and an inner gliding surface, the first end of the cylinder being open for reception of the syringe plunger, the syringe cylinder and the syringe plunger together defining a filling volume within the syringe cylinder of less than 5 ml, the syringe plunger being movable within the syringe cylinder by means of the piston rod;
   a grip formed proximate the first end of the syringe cylinder;
   a tapered syringe head having an outer surface and walls formed integrally as an extension of the second end of the syringe cylinder, the tapered syringe head being formed from the same material as the syringe cylinder and including a conically tapered portion;

wherein the syringe body is formed of plastic that is gamma-sterilizable and/or ethyleneoxide-sterilizable, without any change causing functional deterioration of chemical and physical properties, in particular brittleness and color;

wherein the walls of the syringe cylinder and the syringe head are so formed with regard to water vapor permeability that they have a permeability of less than 0.08 $g/m^2 \times d$ at the wall thickness of 500 μm, whereby the wall is transparent at least in the area of the syringe cylinder; and an injection needle having a first end extending through and integrated directly into the tapered syringe head and indisconnectably fastened therein and a second end extending out of the tapered syringe head proximate the conically tapered portion of the syringe head; and a protective cap of a soft material covering the injection needle so that the needle pierces the protective cap and is thereby sealed, the cap having an inner side that is in sealing abutment with the outer surface of the tapered syringe head, so that the outer surface of the needle is also sealed, whereby the protective cap is gamma-sterilizable and/or ethyleneoxide-sterilizable, without any change causing functional deterioration.

2. A single use syringe according to claim 1, wherein a portion of the insertion needle is encased in the tapered syringe head.

3. A single use syringe according to claim 2, wherein the portion of the insertion needle that is encased in the tapered syringe head has a non-linear shape so as to provide a positive shape conforming connection between the insertion needle and the tapered syringe head.

4. A single use syringe according to claim 1, wherein a recess is formed in the tapered syringe head and the insertion needle is glued into the recess in the tapered syringe head.

5. A single use syringe according to claim 1, wherein tapered syringe head includes support elements in the form of ridges molded into the tapered syringe head.

6. A single use syringe according to claim 1, wherein the outer surface of the tapered syringe head includes a collar portion, whereby the inner side of the cap is in sealing abutment with the collar portion of outer surface of the tapered syringe head, so that the outer surface of the needle is also sealed.

7. A single use syringe according to claim 1, wherein the syringe cylinder includes an inner and outer layer made of different plastics and wherein one of the layers acts as a barrier to oxygen diffusion and the other layer blocks diffusion of water vapor.

8. A single use syringe according to claim 7, wherein one of the plastic layers consists of a cyclic olefin copolymer (COC).

9. A single use syringe according to claim 7, wherein a further layer of metallic, ceramic or glassy material is provided between the inner and outer layers made of different plastics.

10. A single use syringe according to claim 1, wherein the syringe cylinder and the tapered syringe head are provided with an inner layer made of a metallic, ceramic or glassy material.

11. A single use syringe according to claim 1, wherein the syringe cylinder and the tapered syringe head are provided with an outer layer made of a metallic, ceramic or glassy material.

12. A prefillable, low-particle, sterile, single use syringe for the injection of preparations having a filling volume of less than 5 ml, the syringe comprising:

a syringe plunger;

a piston rod connected to the syringe plunger; and a one-piece plastic syringe body, the syringe body including:

a syringe cylinder portion having a first end and a second end and inner walls defining a cylinder portion interior and an inner gliding surface, the first end of the cylinder portion being open for reception of the syringe plunger, the syringe cylinder portion and the syringe plunger together defining a filling volume within the syringe cylinder portion of less than 5 ml, the syringe plunger being movable within the syringe cylinder portion by means of the piston rod;

a grip portion formed proximate the first end of the syringe cylinder portion;

a tapered syringe head portion having walls formed integrally as an extension of the second end of the syringe cylinder portion, the tapered syringe head portion being formed from the same plastic material as the syringe cylinder portion;

an injection needle having a first end extending through and integrated directly into the tapered syringe head portion and a second end extending out of the tapered syringe head portion; and a protective cap of a soft material covering the injection needle so that the needle pierces the protective cap and is thereby sealed, the cap having an inner side that is in sealing abutment with the walls of the tapered syringe head portion, so that the outer surface of the needle is also sealed.

13. A single use syringe according to claim 12, wherein a portion of the insertion needle is encased in the tapered syringe head portion and the portion of the insertion needle that is encased in the tapered syringe head portion has a non-linear shape so as to provide a positive shape conforming connection between the insertion needle and the tapered syringe head portion.

14. A single use syringe according to claim 12, wherein the walls of the syringe cylinder portion and the syringe head portion are so formed with regard to water vapor permeability that they have a permeability of less than $0.08 \text{ g/m}^2 \times \text{d}$ at the wall thickness of 500 $\mu$m, whereby the wall is transparent at least in the area of the syringe cylinder portion.

15. A single use syringe according to claim 12, wherein the outer surface of the tapered syringe head portion includes a collar portion, whereby the inner side of the cap is in sealing abutment with the collar portion of outer surface of the tapered syringe head portion, so that the outer surface of the needle is also sealed.

16. A single use syringe according to claim 12, wherein the syringe cylinder portion includes an inner and outer layer made of different plastics and wherein one of the layers acts as a barrier to oxygen diffusion and the other layer blocks diffusion of water vapor.

17. A single use syringe according to claim 16, wherein one of the plastic layers consists of a cyclic olefin copolymer (COC).

18. A single use syringe according to claim 16, wherein a further layer of metallic, ceramic or glassy material is provided between the inner and outer layers made of different plastics.

19. A single use syringe according to claim 12, wherein the syringe body is formed of plastic that is gamma-sterilizable and/or ethyleneoxide-sterilizable, without any change causing any change in brittleness and color.

20. A single use syringe according to claim 12, wherein the protective cap of a soft material covering the injection needle is formed of a material that is gamma-sterilizable and/or ethyleneoxide-sterilizable, without any change causing functional deterioration.

* * * * *